United States Patent [19]

Postle et al.

[11] Patent Number: 4,649,026

[45] Date of Patent: Mar. 10, 1987

[54] DIAGNOSTIC STRIPS

[75] Inventors: Stephen R. Postle, Wilmslow; Peter J. Elton, Macclesfield; David P. Gregory, Wilmslow, all of England

[73] Assignee: Ciba-Geigy AG, Basle, Switzerland

[21] Appl. No.: 796,346

[22] Filed: Nov. 8, 1985

[30] Foreign Application Priority Data

Nov. 15, 1984 [GB] United Kingdom ................. 8428876

[51] Int. Cl.$^4$ ....................... G01N 1/48; G01N 21/06; B01D 13/02; C25D 13/00
[52] U.S. Cl. .................................. 422/56; 204/182.8; 204/299 R; 422/57; 427/2; 435/22; 436/86
[58] Field of Search ........................ 204/182.8, 299 R; 422/56, 57; 427/2, 289, 293; 435/22; 436/86

[56] References Cited

U.S. PATENT DOCUMENTS 4,415,428 11/1983 Nochumson et al. .......... 204/299 R
4,559,120 12/1985 Royse et al. .................... 204/299 X Primary Examiner—Michael R. Lusignan
Attorney, Agent, or Firm—Wenderoth, Lind & Ponack

[57] ABSTRACT

A method of preparing a diagnostic strip coated with agarose which comprises preparing a roll of web material so that an aqueous silver halide emulsion can adhere thereto on one side thereof, but which does not have a gelatin or any other proteinaceous layer on the prepared side then coating on the prepared side of the web by a continuous web coating method a layer of an aqueous agarose solution at a temperature of at least 40° C., drying the coated agarose layer to provide a dried layer thickness of from 0.1 to 100 μm which is dry to touch, but which comprises 10 to 50% w/w solids and cutting the coated web into strips of the required size.

14 Claims, No Drawings

DIAGNOSTIC STRIPS

This invention relates to strip material of use in electrophoresis and similar techniques such as immunoelectrophoresis, affinity electrophoresis and iso-electric focusing. Such strips are hereinafter referred to as diagnostic strips even though they may be used in preparation techniques.

Agarose, a polysaccharide derived from agar-agar, itself derived from seaweed, has been used as a medium in which to effect such electrophoretic separations. Agarose forms like agar-agar a stiff jelly when dissolved in water and dried. Kits for preparing agarose plates have been available for some years, such kits include agarose powder and dishes in which to form the agarose jelly. Likewise agarose cast on to glass plates with a coating thickness of about 0.5 mm have also been available. However, the preparation of agarose in dishes using a kit is both time consuming and expensive. On the other hand comparatively thick layers of agarose cast on glass plates are even more expensive. Thus the use of agarose has been severely restricted. However we have found a method of preparing diagnostic strips coated with a thin coating of agarose which are easy to prepare in large quantities which can then be dried for ease of handling, but which when soaked in a buffer or like solution can then reswell to provide a medium which can be used in electrophoresis and similar techniques.

According to the present invention there is provided a method of preparing a diagnostic strip coated with agarose which comprises preparing a roll of web material so that an aqueous gelatino silver halide emulsion can adhere thereto on one side thereof, but which does not have a gelatin or any other proteinacious layer on the prepared side then coating on the prepared side of the web by a continuous web coating method a layer of an aqueous agarose solution at a temperature of at least 40° C., drying the coated agarose layer to provide a dried layer thickness of from 0.1 to 100 μm which is dry to touch but which comprises 10 to 50% w/w solids and cutting the coated web into strips of the required size.

Preferably the percentage of solids in the dried layer is from 15 to 30% w/w and most preferably about 20% w/w.

If the percentage of solids is above 50% the layer is tacky and cannot be handled without damage. If the percentage of solids is below 10% then the dried layer when soaked in water followed by a buffer, which is the preferred method of reconstituting the layer before use, will not reconstitute correctly and thus the material cannot be used for any of the techniques hereinbefore listed.

The web material may be a web of paper material which has been sized to retard the absorption of water into the base, the sizing agent used being non-proteinacious, but being sufficiently hydrophilic in nature to allow the web to be coated with an agueous gelatino silver halide emulsion. The web material may be polyethylene laminated paper wherein one side has been corona discharge treated so as to render this side receptive to an aqueous gelatino silver halide emulsion layer.

Preferably, however, the web material is a film material of the type used as a film base for photographic films, but which has no gelatin subbing layer. Such a film material may be cellulose triacetate or cellulose acetate-butyrate which has been surface hydrolysed to make it receptive to an aqueous gelatino silver halide emulsion layer.

More preferably the web material is a biaxially oriented polyester film material which has been prepared by a process wherein the unoriented polyester in web form is oriented in one direction in a stentor, a latex copolymer is then coated on one surface at least of the polyester, orientation of the polyester in the other direction is completed together with a heat-setting procedure. In some cases a corona-discharge treatment of the coated polymer surface is then carried out. Thereafter the agarose solution is coated on the copolymer surface of the biaxially oriented polyester film.

Preferably, the copolymer used comprises up to 10%, and most preferably 0.5 to 9%, by weight of itaconic acid.

Suitable copolymers for use in this method are described in [British patent] specifications Nos. 1540067, 1583343 and 1589926. In methods described in these specifications corona discharge treatment of the biaxially oriented polyester is required to obtain the best adhesion after aqueous coating solution.

Another suitable copolymer is described in G B specification No. 1,571,583, but in this case no corona discharge treatment of the copolymer layer is required to render the surface receptive to an aqueous coating solution layer.

Most preferably the copolymer is a styrene based copolymer.

Coatings having a dried thickness of over 100 μm can also be prepared by this method but such coatings are unnecessarily wasteful in agarose because coatings as thin as 1 to 10 μm have been found to function very well as diagnostic strips.

Various additives may be added to the agarose solution before it is coated. Such additives include wetting agents as coating aids. Humectants for example glycerol, which help to plasticise the coated layer. Additives for example sorbitol and galactomannan which help to improve the water-solubility of the agarose may also be used.

The strips prepared by the method of the present invention are treated in a liquid before use to swell the agarose layer. This liquid is usually water followed by an aqueous buffer. To aid the swelling of the agarose layer additives for example urea may be added to the agarose coating solution. Urea affects the gel strength of the agarose coating and thus if this is not considered to be desirable swelling aids may be added to the liquid which causes the agarose to swell.

When the coated agarose strips are to be used for iso-electric focusing ampholytes, for example mixtures of compounds which contain amide and carboxylic acid groups, may be added to the agarose solution. However, such ampholytes may alternatively be added to the swelling liquid.

Continuous web coating machines which can be used to coat the agarose solution onto the web include any of the coating machines used to coat size solutions onto paper web and any of the machines used to coat gelatin solutions onto photographic base materials. Such coating machines include slot and trough coating machines with or without air blade or doctor bar layer thickness controlling devices. Also cascade and curtain coating machines may be employed as well as gravure and reverse gravure coating machines.

The agarose aqueous solution may be prepared by adding the requisite amount of agarose powder to water and allowing the mixture to stand for one hour. The mixture is then heated rapidly with efficient stirring to above 95° C. and held at the elevated temperature for 15 minutes or until all the powder has dissolved. This is shown by a considerable reduction in turbidity of the solution. The temperature is then lowered with constant stirring to 5° C. above the desired coating temperature (which is usually about 55° C.) and placed in a thermostated storage vessel until it is coated. The actual coating temperature above 40° C. depends on the type of agarose used and on the use of the diagnostic strips.

Agarose is a purified linear galactan hydrocolloid solid which is isolated from agar or recovered directly from agar bearing marine algae. Different agarose preparations vary significantly with respect to their physical and chemical properties.

The physical and chemical properties are influenced by the source of seaweed, including location and stage of growth cycle, the recovery procedure and the process used to isolate the agarose.

Properties such as gelling temperature, gel strength, porosity and electroendosmosis can be adjusted by blending two or more batches. The gelling and melt temperatures are related to methoxyl content of the agarose and properties of agarose can be influenced by incorporating hydroxyethyl groups; e.g. Miles Seaplaque Agarose. Agarose gels are not absolutely clear due to regions of microcrystallinity. Low concentrations of urea and polyethylene glycol reduce turbidy but gel strength is reduced. Although predominantly neutral the agarose matrix contains some anionic residues, e.g. sulphate and pyruvate. Associated with those residues are hydrated counter ions. When an electric current is applied counter ions migrate towards the cathode carrying water of hydration and any neutral sample molecules with them, this is known as electroendosmosis. This is beneficial in counter electrophoresis diagnostic techniques, though not in Isoelectric Focusing. Isoelectric Focusing takes advantage of the fact that each protein has a different pH at which it is electrically neutral; its Isoelectric point (pI). Proteins are separated according to pI by electrophoresis on a gel in which a stable pH gradient has been generated by incorporation of ampholytes. Ampholytes can be mixtures of amides and carboxylic acid groups which come to rest in order of pI when subjected to an electric field and each of which maintains a local pH corresponding to its pI by virtue of a strong buffering capacity. The ampholytes can be incorporated during formulation or in swelling of the dried agarose layer with little effect of degree of separation achieved.

Many other electrophoretic and immunology, cell culture and cloning techniques can be used with agarose layers having varying physical and chemical properties, e.g. serum protein electrophoresis, nucleic acid electrophoresis, separation by molecular weight, 2D electrophoresis, cell and virus electrophoresis, Ouchterlony gel diffusion, radial immunodiffusion, immunoelectrophoresis, Laurell rockets and crossed immunoelectrophoresis, counter electrophoresis and antigen-antibody overlays. The dried agarose layers can easily be swollen by soaking in a suitable solvent. The degree of swelling is dependent on the type and quantity of agarose coated, the temperature of swelling, the type and pH of the solvents used. Agarose coatings for electrophoretic techniques are usually soaked in a more concentrated form of the buffer to be used in the protein separation.

It is an important feature of the strips prepared by the method of the present invention that no gelatin subbing layer be present between the polyester base and the agarose layer. As gelatin is protein based this interferes greatly with protein separation techniques as it stains badly and prevents identification of separated proteins. In the preferred method of the present invention the dried latex styrene based copolymer applied at the interdraw stage provides a hydrophilic layer onto which the agarose coating solutions can be applied and to which it can adhere. Preferably the film base after full orientation and heat setting is corona discharge treated. This adds in the adherence of the agarose solution to the base. However it is not always necessary.

The following example will serve to illustrate the invention:

EXAMPLE

A polyester polyethylene terephthalate film base support prepared as described in Example 11 of British patent specification No. 1540067, except that no silver halide emulsion was coated onto the corona discharge treated film surface, was used.

An agarose aqueous solution was prepared as follows:
Agarose (Serva Zero EE0 ®): 20 g
Wetting Agent (Olin 10G ®): 2.0 g
Water to 1 liter The agarose was soaked in the water for 60 minutes in the presence of the wetting agent. The mixture was then heated strongly with vigorous stirring until it boiled at 96° C. The temperature was lowered to 92° C. and maintained at this temperature until the opaque appearance of the solution cleared. The temperature of the solution was reduced to 60° C. whilst stirring constantly and then transferred to a thermostated coating vessel. The solution was then slot coated onto the polyester film base as just described. The film base was carried passed the coating slot at 15 feet per minute and the volume per unit area of solution coated on the film base was 1.6 cm$^3$ dm$^{-2}$. The temperature of the coating solution when coated was 55° C.

The coating was then chilled to set the agarose and air impingment dried to 20% solids w/w. The thickness of the coated dried agarose layer was 10 μm and the layer was not tacky.

The film base coated with the dried agarose layer was then chopped into strips 6×18 cm in length which is a suitable size for diagnostic strips.

Both wet and dry adhesion tests as described in B. P. No. 1540067 were carried out and in both tests the agarose layer adhered very well to the film base.

One of these strips was used in an electrophoresis test to show what proteins were present in a sample of human serum. A Shandon 600 Electrophoresis Chamber was employed. A strip as just prepared was punched to provided strip retaining holes.

The strip was then soaked in water for 10 minutes and then placed in an aqueous buffer bath (pH 8.6, 0.05M) for 10 minutes to swell the agarose layer. Excess buffer was removed and the strip placed in the electrophoresis chamber, each end of the strip dipping into a bath of 0.025M buffer.

A small volume of the serum was applied to one end of the strip using a filter paper. Small samples containing known serum proteins were placed in a line along the strip at the same end.

A constant current of 3 mA which is ½ mA per cm width of strip was applied for five minutes. The agarose strip was then removed from the chamber and placed in a 10% Ponceau Red solution (C.I. Nr. 27195) to stain the proteins.

Adventitious staining was then removed by soaking in dilute acetic acid for ten minutes, leaving only the separated proteins stained. The strip was soaked in a solution of 10% dilute acetic acid in 90% methanol and the strip dried.

The dried strip showed the various proteins present in the serum sample separated along the length of the strip. Their identity was established by comparison with the known proteins which has also separated along the length of the strip.

This test shows that the strips prepared by the present invention even though the coated layer of agarose was very then are of use in an electrophoresis protein separation technique.

We claim:

1. a method of preparing a diagnostic strip coated with agarose which comprises preparing a roll of web material so that an aqueous silver halide emulsion can adhere thereto on one side thereof, but which does not have a gelatin or any other proteinous layer on the prepared side then coating on the prepared side of the web by a continuous web coating method a layer of an aqueous agarose solution at a temperature of at least 40° C., drying the coated agarose layer to provide a dried layer thickness of from 0.1 to 100 μm which is dry to touch, but which comprises 10 to 50% w/w solids and cutting the coated web into strips of the required size.

2. A method according to claim 1 wherein the percentage of solids in the dried layer is from 15 to 30% w/w.

3. A method according to claim 2 wherein the percentage of solids in the dried layer is about 20% w/w.

4. A method according to claim 1 wherein the dried coating thickness is from 1 to 10 μm.

5. A method according to claim 1 wherein the web material is a web of polyethylene laminated paper, the side of which is to be coated has been corona discharge treated.

6. A method according to claim 1 wherein the web material is biaxially oriented polyester which has been prepared by a process of orienting in one direction a web of unoriented polyester, supplying to one surface of the polyester a copolymer latex, completing the orientation and heat setting the coated polyester.

7. A method according to claim 6 wherein the copolymer comprises up to 10% by weight of itaconic acid.

8. A method according to claim 6 wherein the copolymer is a styrene based copolymer.

9. A method according to claim 6 wherein the polyester web after biaxial orientation is corona discharge treated on the side coated with the copolymer.

10. A method according to claim 1 wherein aqueous agarose solution is coated onto the web using a slot, trough, cascade or curtain coating machine.

11. A method according to claim 1 wherein a wetting agent is added to the aqueous agarose coating solution.

12. A method according to claim 1 wherein a swelling agent is added to the aqueous agarose solution.

13. A method according to claim 1 wherein an ampholyte is added to the aqueous agarose solution.

14. A diagnostic strip coated with agarose when prepared by the method claimed in claim 1.

* * * * *